United States Patent [19]

Merz et al.

[11] Patent Number: 4,573,915

[45] Date of Patent: Mar. 4, 1986

[54] OCCLUSIO-REFERENTIAL ARTICULATOR

[76] Inventors: Eugen Merz, Alte Landstrasse 94, CH 8803 Rüschlikon; Sami Sandhaus, 4, Avenue de Provence, CH-1024 Lausanne; Norbert Troger, Brüelweg 38, CH-4147 Aesch, all of Switzerland

[21] Appl. No.: 648,890

[22] Filed: Sep. 10, 1984

[30] Foreign Application Priority Data

Sep. 16, 1983 [CH] Switzerland ............... 5047/83

[51] Int. Cl.$^4$ ............................................ A61C 11/00
[52] U.S. Cl. ........................................ 433/64; 433/55; 433/65
[58] Field of Search .................. 433/54, 55, 56, 57, 433/58, 59, 60, 61, 62, 63, 64, 65

[56] References Cited

U.S. PATENT DOCUMENTS

| 2,613,440 | 10/1952 | Murray et al. | 433/55 |
| 2,621,407 | 12/1952 | Schlesinger | 433/65 |
| 2,959,857 | 11/1960 | Stoll | 433/55 |
| 4,391,589 | 7/1983 | Monfredo et al. | 433/63 |

FOREIGN PATENT DOCUMENTS 191238  1/1923  United Kingdom ............... 433/58

Primary Examiner—John J. Wilson
Attorney, Agent, or Firm—Ladas & Parry

[57] ABSTRACT

It comprises an upper maxillary support (14) and a lower maxillary support (47). The lower support comprises a movable piece (27) on a rack (24) supporting an arm (31) mounted to slide vertically on the movable piece (27) with a limited travel for its vertical displacement on the movable piece (27). The arm (31) carries two intersecting orthogonal slideways (41,42). The upper slideway (42) carries a table (47) mounted on a spherical knuckle. The articulator allows accurate recording and accurate reproduction of the occlusion position of the maxillaries and of the closure of the mandible, without seeking to reproduce the condylar articulations.

10 Claims, 4 Drawing Figures

OCCLUSIO-REFERENTIAL ARTICULATOR

The subject of the present invention is an occlusio-referential articulator allowing an analytical breakdown of the mandibular movement, comprising a frame on which are mounted an upper plane support for the mold of the upper maxillary, extending approximately horizontally and fixed in the position of use, a movable lower plane support for the mold of the lower maxillary, and means for displacing and positioning the lower plane support relative to the upper plane support both perpendicularly to the upper support and parallel to this support.

Many types of articulator have been proposed for the purpose of reproducing the movements of the mandible, previously measured on an individual, in relation to the upper maxillary, to enable practitioners, particularly prosthetists, to make a dental prosthesis conforming to the kinematics of the particular individual. The articulator is intended to support molds of the lower and upper jaws.

In known articulators, attempts have been made, in general terms, to reproduce the condylar articulation more or less approximately. The articulators described in French Patent Nos. 2,387,027, 2,278,312 and 2,498,924 are concerned with this. In these devices, the support of the lower maxillary is in the form of a right-angled piece, and for reasons of convenience it is the support of the upper maxillary which is articulated about an axle on this right-angled support. If only because of this reversal, the natural movement of the mandible is not reproduced.

French Patent No. 2,188,442 describes an articulator having five degrees of freedom, each corresponding to a pure movement or to a single component of the natural movements in order to achieve an exact reproduction of these movements. This articulator attempts to fulfil this aim by means of a lower support bent like a mandible and articulated by means of two spheres presumed to reproduce the articular condyles of the mandible. Although the construction of this articulator is relatively simple, nevertheless it is complicated to use. The movements are recorded by means of three feet in wax or resin pellets. The recording pellets or cups are subsequently used to control the displacement of the mandible. Recording and control are therefore purely analogical. Moreover, the spheres of the articulations reproduce the condylar articulatons only imperfectly.

There has already been a proposal to work with a fixed upper maxillary support, as occurs naturally, and with a lower maxillary support movable in all directions (European patent application No. 0,025,201). In this articulator, the movable support is mounted on six electronically controlled jacks. Such an articulator requires complicated electronics which are costly for small production series.

A purely mechanical articulator with a fixed upper support is described in European patent application No. 0,054,600. The mandible support is displaceable vertically by means of a vertical screw and a knurled nut. It possesses a movable part in the form of a right-angled piece, comprising two vertical rods interacting individually with two rotary sockets, the movement of which is presumed to reproduce the sagittal movement of the mandible. The occlusion position is recorded by means of a reading of the angular position of the two rotary sockets.

This system, like all the other prior mechanical systems, is based on a common principle, according to which the aim is to reproduce the natural condylar articulations. These articulations, however, are complex, and moreover the mechanisms seeking to reproduce them incorporate an error arising from a misunderstanding of the exact and complete movement of the mandible during its closure. In fact, although the mandible does indeed execute a pivoting movement at the level of the condylar articulations during its closure on the upper maxillary, the last phase of this closing movement, more specifically the last millimeters of this closing movement, no longer correspond to a rotary movement, but to a movement of vertical or slightly oblique translation.

The present invention firmly rejects the idea of reproducing the form of the mandible and its condylar articulations and adopts the aim of allowing accurate recording and accurate reproduction of the occlusion position of the maxillaries and of the closure of the mandible, without seeking to reproduce the condylar articulations. The articulator to be produced should also be relatively simple in mechanical terms, easy to manufacture, easy to use and capable of being positioned quickly and accurately.

The articulator according to the invention is defined in that the lower support comprises a movable piece on a rack approximately perpendicular to the upper plane support and supporting an arm which extends perpendicularly to the rack and is mounted to slide vertically on the said movable piece with a limited travel and which is provided with a manually actuated cam for its vertical displacement on the said movable piece, this arm carrying two intersecting orthogonal slideways, each provided with a graduated actuating screw, the upper slideway carrying a spherical knuckle which supports a plane table possessing positioning means for the mold of the lower maxillary or its support.

The slight travel of the arm on the movable piece supporting it makes it possible to reproduce the last phase of the closing movement of the mandible. Because an elastic mounting is provided, it is even possible to obtain automatic displacement of the arm in the occlusion position, when laterality is modified, for example during an examination of the diduction.

The two intersecting orthogonal slideways make it possible to record two rectangular coordinates of a central position in a simple and accurate way. As regards the spherical knuckle, this makes it possible to obtain the sagittal inclination immediately or make any corrections in any direction, in order to achieve a perfect occlusion. The position of the knuckle can be recorded by means of a circular graduation or by means of graduted meridians and/or parallel lines marked out on the spherical knuckle. All the movable elements are preferably equipped with a locking handle.

The assembly consisting of the two supports forms a rigid whole which is preferably mounted pivotally between two columns and which is lockable in an oblique position so as to make the practitioner's work easier.

According to a preferred alternative form, two retractable and orientable tool-holder arms are mounted on the extension of two columns, thus converting the appliance into an ergonomic work station.

Other advantages of the articulator according to the invention will emerge from a reading of the description of an embodiment, made with reference to the attached drawing in which.

Figure 1:
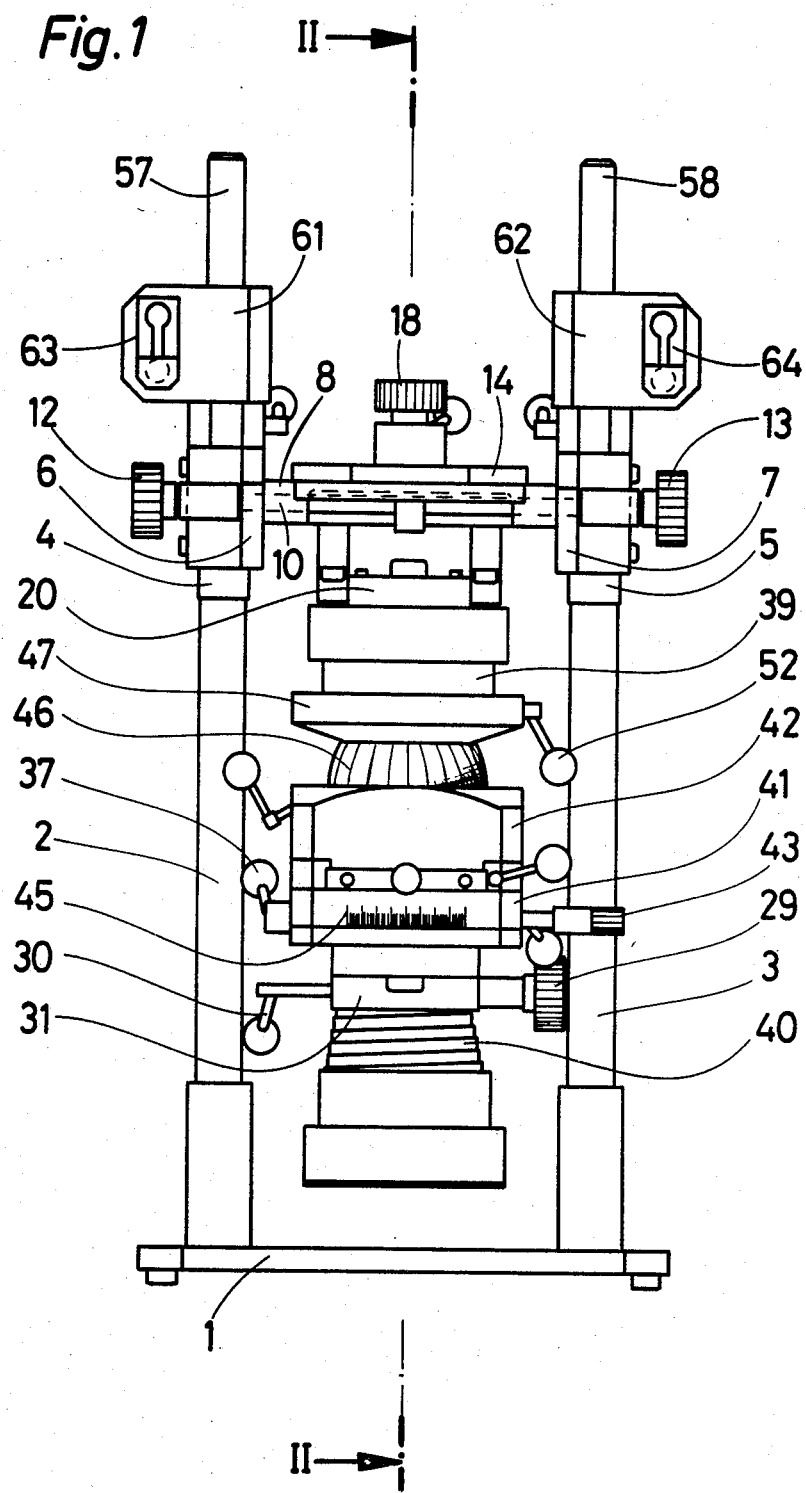
FIG. 1 shows a front elevation view of the articulator.

The articulator comprises a frame consisting of a platform 1 provided with rubber feet carrying two columns 2 and 3, on which the elements of the articulator are mounted. Fastened to two bearing surfaces 4 and 5 of the columns 2 and 3 are two vertical right-angled pieces 6 and 7 which form a bracket and between which is mounted a horizontal strut 8 pivoting about an axle 9. A second axle 10 passes through the strut 8 and also passes through the right-angled pieces 6 and 7 via two slots 11 in the form of an arc of a circle centered on the axle 9. The strut 8 can thus pivot about its axle 9 through an angle corresponding to the arc of the slot 11. It can be locked in the desired position by means of two knurled nuts 12 and 13. A plate 14 articulated about the axle 10 constitutes the upper plane support for the mold of the upper maxillary. In the working position, this plate 14 rests on the upper plane face of the strut 8. It can be locked in this position by means of a handle 15 which actuates a locking finger 16 engaging under the axle 9. The plate 14 also carries on its lower face a removable plate 17 intended for receiving the mold of the upper maxillary. This plate is retained by a knurled screw 18 and positioned by means of a pin 19.

Figure 4:
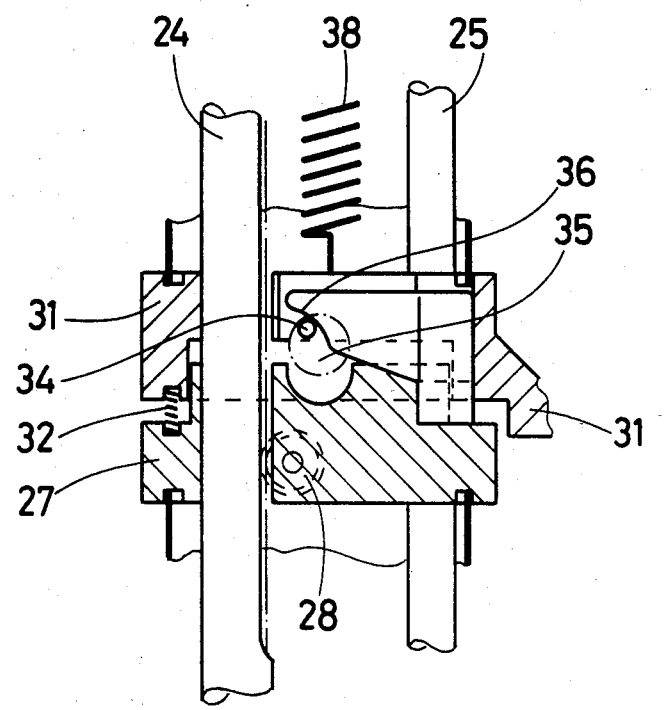
FIG. 4 shows in section a detail of the arm of the lower support.

The axle carries a plate 20 in the form of a right-angled piece, which has a variable orientation determined by a stop screw 21 screwed into an extension 22 of the cross member 8. A block 23 is fastened under the plate 20 by means of a screw. This block 23 is integral with a rack 24 and with two guide colums, one 25 of which can be seen in FIG. 2. The lower ends of the rack 24 and of the guide columns 25 are fastened in a lower block 26. The rack 24 and the columns 25 pass through a movable piece 27, a detailed representation of which is shown in FIG. 4. This movable piece 27 is provided with a horizontal toothed shaft interacting with the toothing of the rack and is capable of being driven by means of a knurled knob 29 (FIG. 1). The movable piece can be locked at the desired height by means of a handle 30 which drives a locking screw acting on the rack 24. The movable piece 27 supports a horizontal arm 31 carrying the lower plane supports for the mold of the lower maxillary. This arm 31 is likewise mounted to slide on the guide columns 25. It is retained approximately 3 mm above the movable piece 27 by four springs, two 32 and 33 of which can be seen in FIG. 2, the other two springs being arranged in the other two corners of the rectangular movable piece 27. The distance between the pieces 27 and 31 is limited by a cam 34 integral with an axle 35 mounted in the arm 31 and interacting with a slope 36 of the movable piece 27. This cam 34 can be actuated by means of a handle 37 (FIG. 1) integral with the shaft 35. The actuation of the cam 34 makes it possible to bring the arm 31 in contact with the movable piece 27, compressing the springs 32, 33. The cam 34 has a stable position, in which the arm 31 remains up against the movable piece 27 without an auxiliary locking means. The movable unit consisting of the movable piece 27 and the arm 31 is also suspended on two weight-compensating springs 38, the upper ends of which are attached to the upper block 23. These springs 38 prevent a rapid and dangerous descent of the movable unit. The rack 24 and the guide columns 25 are protected within two metal bellows 39 and 40 consisting in a known way of a helically wound steel sheet.

The arm 31 carries two slideways 41 and 42 which are superimposed and intersect orthogonally and which are similar to the slideways of a machine-tool table. These slideways 41 and 42 are displaceable respectively by means of two micrometer screws 43 and 44. They each move opposite a graduated scale, such as 45 (FIG. 1).

Mounted on the upper slideway 42 is a spherical knuckle 46 integral with a table 47 constituting the movable lower plane support for the mold of the lower maxillary. This table 47 possesses positioning receptacles 48 and 49 for a removable plate 50, on which the mold of the lower maxillary 51 is fastened. The plates 50 can be locked by means of a horizontal screw which can be actuated by a handle 52. The knuckle 46 is on the one hand mounted in a spherical receptacle 53 of the upper slideway 42 and on the other hand supported by means of a ballbearing 54 via a central column 55, the upper end of which is spherical. A vertical finger 56 mounted on a spring and interacting with a central polar receptacle of the knuckle 46 locates the horizontal position of the table 47 and retains it gently in this position. The plane upper face of the upper slideway 42 has a graduation interacting with at least one index on the knuckle 46, to determine and record the position of the table 47 about a vertical axis. This graduation can be of any type, for example in degrees or completely arbitrary. Furthermore, graduated meridians making it possible to determine and record the inclination of the table 47 relative to the horizontal plane are marked out on the knuckle 46.

Moreover, horizontal arms 59 and 60 are mounted on the cylindrical extensions 57 and 58 of the columns 2 and 3. These arms 59 and 60 are mounted to slide in supports 61 and 62, themselves mounted rotatably on column 57 and 58. All these mountings are made by means of bearings. These arms 59 and 60 have at their ends clips 63 and 64 (FIG. 1) for fastening tools, for example a drill 13, or measuring instruments, such as a comparator.

It is particularly easy to use this articulator. To secure the mold 65 of the upper maxillary, the upper support 14 can be raised to a vertical position about the axle 10. Moreover this raised position exposes the table 47 completely, thus making it possible to secure the mold 51 of the lower maxillary on this table 47 with complete freedom.

The upper plate is subsequently turned down and locked by means of the handle 15. This fixed position conforms to the fixed position of the upper maxillary.

The table 47 is subsequently raised by means of the knurled nut 29 and the rack 24. The recording of the mandibular function of the patient, whose maxillary molds are mounted on the articulator, is carried out very simply and accurately by means of the two orthogonal slideways 41 and 42 and by means of the knuckle 46. These three movable pieces make it possible to put the table 47 in any position, within a certain range of course, and record the position of this table by simply reading the graduated scales.

It is thus possible to study and record the sagittal inclination and laterality without difficulty and with great accuracy.

Figure 2:
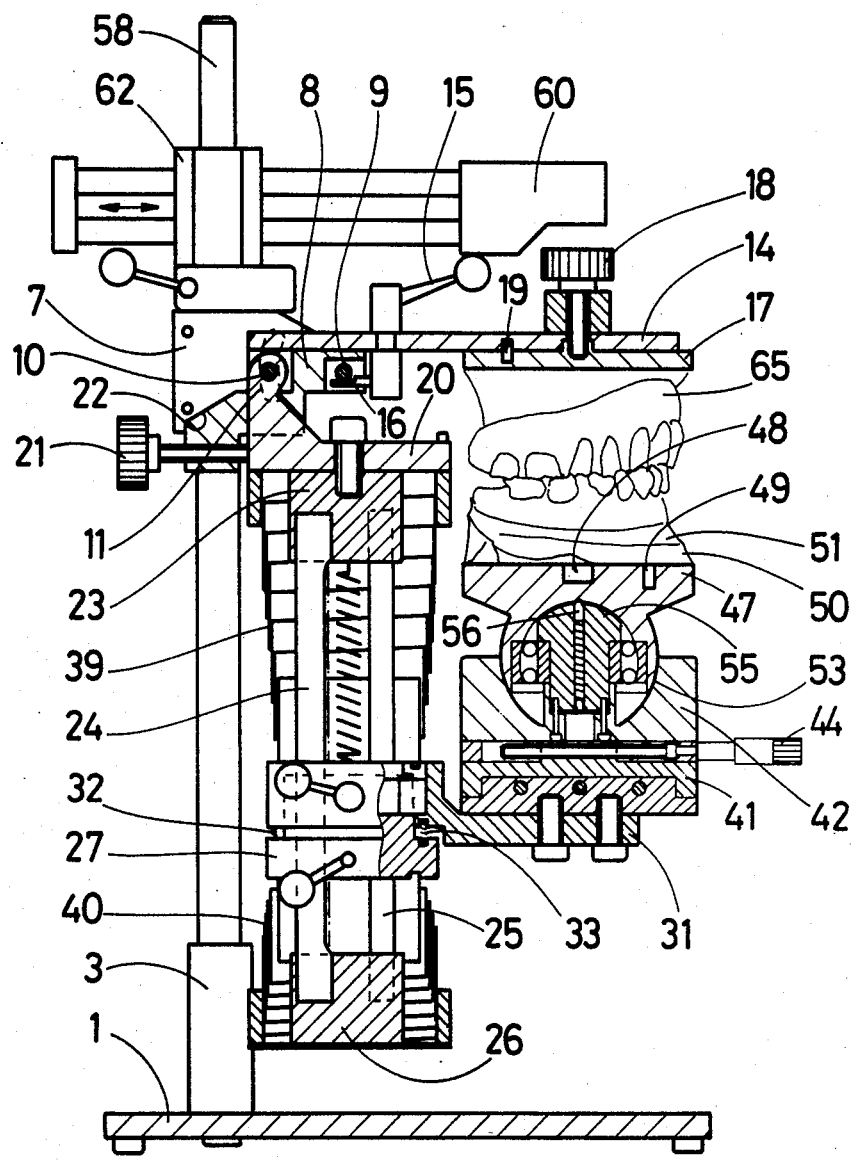
FIG. 2 shows a view in axial section along the line II—II of FIG. 1.
Figure 3:
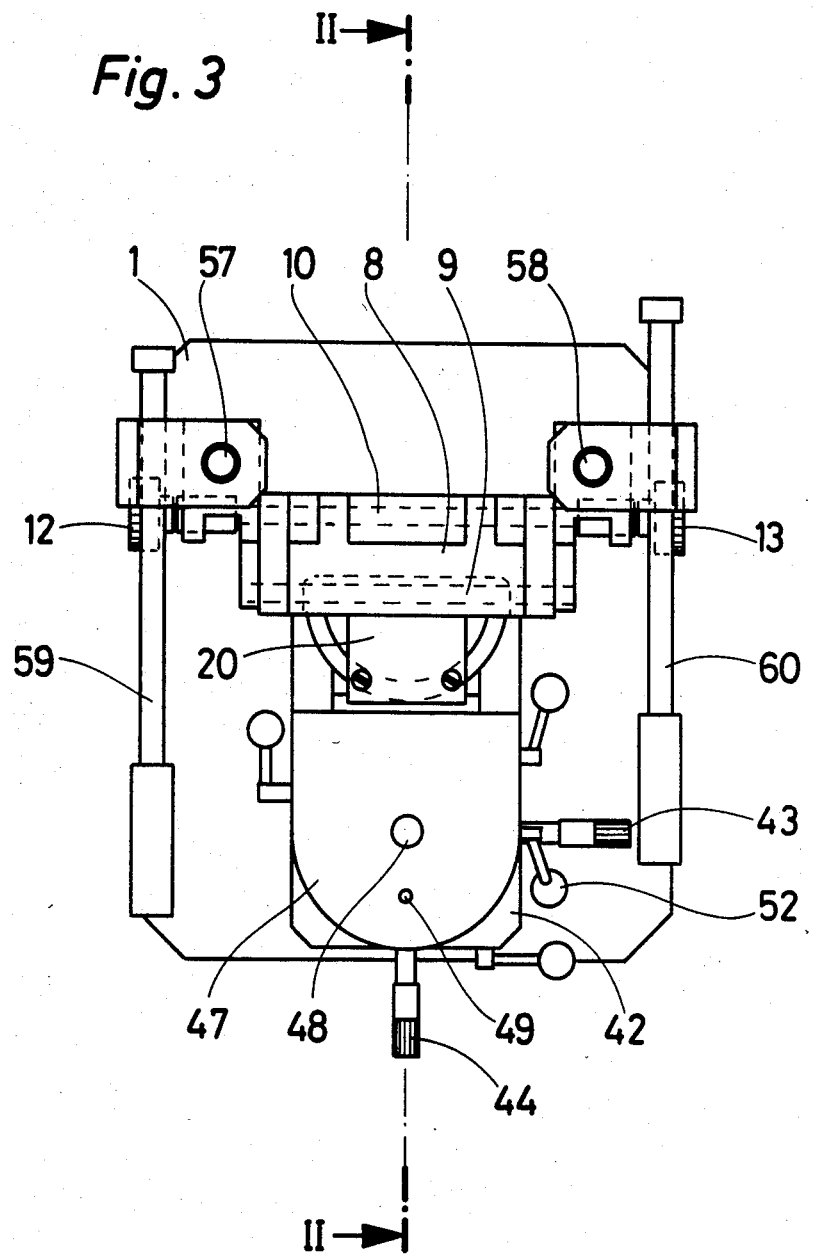
FIG. 3 shows a plan view.

For tests of mandibular functions, the lower support is pivoted about the axle 10 by means of the knurled screw 21 (FIG. 2). During this pivoting, the arm 31 is first held up against the movable piece 27. The final closing of the jaw is effected by means of the cam 34, that is to say with the release of the arm 31 which is then raised elastically by the springs 32 and 33, this vertical travel corresponding to the identified translational displacement of approximately 3 mm. The advantage of this vertical displacement is that it is elastic, that is to say it takes place gently, without the risk of damage to the mold or the prosthesis being checked.

When this closed position has been reached, it is even possible, in some cases, to execute lateral displacements by means of the micrometer screw 43 in order to check the diduction, the teeth of the upper maxillary acting as cams which can push back the teeth of the lower maxillary vertically by compressing the spring 32 and 33 elastically.

It is appropriate to note that the upper articulation about the axle 10 of the support of the lower maxillary is not an essential function, and that this could be omitted, since the displacement of the lower maxillary can be effected completely by means of the rack, the orthogonal slideways 41 and 42 and the knuckle 46.

The articulation of the assembly about the axle 9 can be locked in an oblique position by means of the knurled nuts 12 and 13 and enables the user to work in a convenient inclined position.

The construction described above is of course capable of assuming many alternative forms.

We claim:

1. An occlusio-referential articulator comprising a frame on which are mounted an upper plane support (14) for the mold of the upper maxillary (65), extending approximately horizontally and fixed in the position of use, a movable lower plane support (47) for the mold of the lower maxillary (51), and means for displacing and positioning the lower plane support relative to the upper plane support both perpendicularly to the upper support and parallel to this support, wherein the lower support (47) comprises a movable piece (27) on a guide means (24) approximately perpendicular to the upper plane support (14) and said movable piece (27) is mounted to slide on two guide columns (24,25) of said guide means (24) and is suspended on at least one weight-compensating spring (38) and said movable piece (27) supports (and supporting) an arm (31) which extends perpendicularly to said guide means (24) and is mounted to slide vertically on the said movable piece (27) with a limited travel and which is provided with a manually actuated stop means (34) for its vertical displacement on the said movable piece (27), said arm (31) carrying two intersecting orthogonal slideways (41),(42), each provided with a graduated actuating screw, the upper slideway (42) carrying a spherical knuckle (46) which supports a plane table (47) possessing positioning means (48,49) for the mold of the lower maxillary or its support (50).

2. An articulator as claimed in claim 1, wherein the said arm (31) is supported by the said movable piece (27) by means of springs (32,33), and wherein the said stop means (34), the actuating axle of which is integral with the said arm (31), interacts with a bearing surface (36) of the said movable piece (27) so as to compress the said springs (32, 33).

3. An articulator as claimed or claims 1 to 2, which incorporates means of locking each movable member.

4. An articulator as claimed in one of claim 1, wherein the two supports (14, 47) and the guide means (24) constitute an assembly mounted pivotally about a horizontal axle (10), locking means being provided to lock the assembly in an ergonomic working position.

5. An articulator as claimed in claim 4, wherein the said assembly is mounted on two columns (2, 3), the extensions of which constitute bearing supports (61, 62) for pivoting and retractable tool-holder arms (59, 60), allowing any prosthetic work, such as drilling, parallel alinement and marking-out, to be executed.

6. An articulator as claimed in claim 1, which incorporates means of recording the position of the spherical knuckle.

7. An articulator as claimed in claim 6, wherein graduated meridians are marked out on the knuckle (46) for determining and recording the inclination of the table (47) relative to the horizontal plane.

8. An articulator as claimed in claim 6, wherein said spherical knuckle (46) is provided with graduated meridians for determining and recording the inclination of the lower plane support (47) relative to the horizontal plane.

9. An articulator as claimed in claim 1, which incorporates means of recording the position of the support of the lower maxillary relative to the support of the upper maxillary by means of plane, angular and spherical coordinates.

10. An articulator as claimed in one of claims 1, which incorporates means for the zero positioning of the said spherical knuckle.

* * * * *